United States Patent [19]

Powell et al.

[11] 4,321,263

[45] Mar. 23, 1982

[54] PSYLLIUM COMPOSITIONS

[75] Inventors: David R. Powell; Vithal K. Patel, both of Baudette, Minn.

[73] Assignee: Rowell Laboratories, Inc., Baudette, Minn.

[21] Appl. No.: 207,600

[22] Filed: Nov. 17, 1980

[51] Int. Cl.$^3$ .................. A61K 9/16; A61K 31/74; A61K 31/79; A61K 35/78

[52] U.S. Cl. .................. 424/195; 424/78; 424/80

[58] Field of Search .................. 424/195, 80, 78

[56] References Cited

U.S. PATENT DOCUMENTS

| | | | |
|---|---|---|---|
| 1,891,697 | 12/1932 | Tuvin | 424/195 |
| 2,043,204 | 6/1936 | Spalding | 424/38 |
| 2,060,336 | 11/1936 | Near et al. | 424/195 |
| 2,095,259 | 10/1937 | Kober et al. | 424/195 |
| 2,132,484 | 10/1938 | Kober | 424/195 X |
| 2,146,867 | 2/1939 | Welin | 424/34 |
| 2,278,464 | 4/1942 | Musher | 424/195 |
| 2,540,253 | 2/1951 | Gakenheimer | 424/78 |
| 2,820,741 | 1/1958 | Endicott et al. | 424/80 |
| 3,136,692 | 6/1964 | Bandelin | 424/80 |
| 3,553,313 | 1/1971 | Tort | 424/80 |

OTHER PUBLICATIONS

Martindale the Extra Pharmacopoeia 27th Ed. (1977) London. Pharm. Press, p. 915-934 esp. p. 926 "Ispaghula", Husk Plantago Ovata Coatings, Psyllium Hydrophillic Mucilloid, pp. 927-928 Povidone (PVP) pp. 929 Psyllium.

Chem. Abstracts 35:6318$^{(4)}$ (1941), 43:8609$^b$ (1949), 48:4775$^e$ (1954).

Chem. Abstracts 48:8486$^i$ (1954), 49:9230$^e$ (1955) 56:1526$^a$ (1962).

*Primary Examiner*—Shep K. Rose
*Attorney, Agent, or Firm*—Millen & White

[57] ABSTRACT

Psyllium powder is rendered substantially instantly and uniformly dispersible in water by wetting the psyllium particles with an alcoholic solution of at least one of polyethylene glycol and polyvinylpyrrolidone and granulating the thus-coated particles. Polyvinylpyrrolidine in the coating reduces the friability of the granules.

16 Claims, No Drawings

PSYLLIUM COMPOSITIONS

BACKGROUND OF THE INVENTION

This invention relates to granulated psyllium compositions which are readily dispersible in water and aqueous beverages.

Powdered husks of the psyllium seed is a common and effective bulk laxative drug. The hydrophilic properties of this natural fibrous laxative causes ingested does to absorb large amounts of water, thus producing bulk and normalizing regularity through proper stool formation.

The single normal adult dose is about 3 grams of psyllium powder which is dispersed by the user in water or an aqueous beverage. Powdered psyllium has very poor wetting capabilities and therefore must be vigorously mixed with aqueous fluids to produce a palatable dispersion.

Historically, psyllium seed preparations have been formulated to contain equal parts of active bulk laxative and a sugar (usually dextrose) as a means of promoting dispersion ease. These 50:50 dilutions are also inconvenient to the user since mixability is still often difficult. Rigorous agitation and/or stirring are required to render the composition palatable and lump free. Moreover, patients on restricted sugar-free or weight controlling diets cannot normally use these products.

Attempts to improve mixability have led to effervescent powder formulas which at best still contain only about 50% of active bulk laxative, are usually high in sugar content and contain significant amounts of sodium or potassium ion, which preclude their use by diabetic patients and patients on low sodium diets.

Pure psyllium powder resists wetting in water or aqueous beverages because of its fine particle size and the inability of water to penetrate the powder mass due to fast surface hydration and swelling. Vigorous agitation in water results in a lumpy dispersion. The lumps, although wetted on their outer surface, contain dry undispersed powder on the inside. Fluid penetration must precede hydration in order to accomplish instant wettability and dispersability.

The wettability of powdered psyllium can be enhanced by diluting the particles with large amounts of a highly water soluble material, e.g., sucrose. The disadvantages of doing so have been discussed above. Moreover, lumping is not totally avoided because in order to do so, the water soluble material must impart dilation to the psyllium powder, viz., the creation of voids between the individual particles which hold them apart long enough to allow the individual particles to become wet rather than agglomerated into clumps. As stated above, sugars have been used for this purpose with limited success. Effervescent sugar-psyllium mixtures self-dilate when carbon dioxide is released upon use. It follows therefore, that air alone should act as a diluent for a bed of pysllium if the bed were properly mechanically dilated.

However, neither dilation alone nor the water solubility of the coating agent ensures rapid and complete dispersibility of powdered psyllium in water and aqueous beverages. Although a number of water soluble or dispersible polymers can be used to achieve dilation of powdered psyllium by conversion thereof into granules in which the psyllium particles are diluted with air voids, instant and complete dispersibility of the resulting product in water and aqueous beverages is rarely achieved employing amounts thereof which could form alcoholic solutions of a viscosity low enough to be used to granulate the psyllium.

A wetting test was developed to show the effect of various polymers on the wettability of psyllium granules produced by wet granulation of psyllium powder with solutions thereof. The time required to completely wet 3.7 g of psyllium ladled onto the surface of 150 ml. of water (or aqueous beverage) in a 65 ml diameter beaker was measured. If greater than 2 minutes was required for wetting, the wetting time was recorded as greater than 120 seconds.

Table I below lists the results of attempts to accomplish more rapid wetting of psyllium with glycerin, which theoretically should enhance dispersibility of the psyllium by increasing the surface wetting of the psyllium powder. Alcoholic (anhydrous ethanol) solutions of glycerin with or without Tween 80, a surface active agent, were added to psyllium powder. Thorough mixing of the wetted powder insured total distribution of the ingredients. The alcohol was evaporated, the powders were sized and treated. It was found that even when a strong wetting agent was added, glycerin did not enhance wettability. Only with equal parts of psyllium and dextrose did a mixture of glycerin and wetting agent produce fast wetting because although glycerin should have been a good wetting bridge between psyllium and water, it did not impart any dilation to the powder mass. In fact, the quick hydration at the powder-water interface actually impeded penetration of the water and complete wetting of all the particles was prevented. By dilution with 50% dextrose, dilation of the psyllium in effect was accomplished and penetration of the water preceded hydration and, with the aid of the glycerin and wetting agent, fast lump-free wetting occurred. However, the resulting product had the other disadvantages discussed above.

TABLE I

| Psyllium | Contents % Dextrose | Glycerin | Tween 80 | Wetting Time (sec.) |
|---|---|---|---|---|
| 50 | 50 | — | — | >120 |
| 50 | 48.4 | 1.5 | 0.1 | 10 |
| 75 | 23.4 | 1.5 | 0.1 | >120 |
| 98.4 | 0 | 1.5 | 0.1 | >120 |
| 96.9 | — | 3.0 | 0.1 | >120 |
| 97.9 | — | 2.0 | 0.1 | >120 |
| 97.0 | — | 3.0 | — | >120 |
| 95.0 | — | 5.0 | — | >120 |

Table II below gives the wetting times obtained with various polymeric and other materials used to achieve mechanical dilation by wet granulation of the psyllium powder from an alcoholic (95% denatured) solution of the selected material. Agglomeration of psyllium particles effectively achieved mechanical dilation by dilution with air voids. The concentrations thereof employed were dictated by the viscosity of the solutions thereof or toxicity considerations. Although dilation was accomplished in all cases except one (Pluronic a S.A.A.), fast aqueous penetration and uniform wetting was only occasionally achieved.

TABLE II

| Psyllium Content | Polymer | |
|---|---|---|
| 100% | None | >120 |
| 98% | Methocel E-15 2% | >120 |

TABLE II-continued

| Psyllium Content | Polymer | |
|---|---|---|
| 99.8% | Carbopol 0.2% | >120 |
| 99% | Methocel E-15 1% | 90 |
| 99% | Pluronic F-68 1% | >120 |
| 99% | Gantrez-AN119 1% | >120 |
| 98% | Xanthan Gum 2% | >120 |
| 95% | Sucrose Syrup 5% | >120 |
| 99% | PVP 1% | 22 |
| 99% | PEG 1% (3350) | 30 |

Notwithstanding the foregoing results, we have found that certain of the foregoing polymers can be employed in a wet granulation process at higher concentrations to produce granulated psyllium products which not only have a high psyllium content (greater than 90% and usually at least about 95%) but which are substantially instantly and uniformly dispersible in water and aqueous beverages.

Polyvinylpyrrolidone (PVP) is one of the polymers which proved to be operable at concentrations above about 2%. U.S. Pat. No. 2,820,741 teaches the use of an alcoholic solution of PVP as a granulating agent for water-insoluble materials which are unstable in the presence of water and that PVP aids in the physical disintegration of granules when formed into tablets or filled into capsules. However, it teaches nothing about the effect thereof upon the dispersibility of such granulated materials in water. U.S. Pat. No. 3,725,541 discloses the use of a water insoluble polymer or copolymer of vinylpyrrolidone and powdered sugar to produce a granulated anti-diarrhea product. Other patents which disclose a process of preparing a pharmaceutical by the addition of the active ingredient to an alcoholic PVP solution are U.S. Pat. Nos. 3,089,818; 3,257,277; 3,553,313; 3,673,163; and 4,081,529. We have also found that polyethylene glycol (PEG) is superior to PVP in achieving rapid dispersibility of the psyllium in water at concentrations above about 1.5% by weight of the psyllium. Patents which employ PEG in the preparation of pharmaceutical products are U.S. Pat. Nos. 2,698,822; 2,540,253; 3,308,217; 3,862,311; 3,932,613; and 4,151,273. Gakenheimer (U.S. Pat. No. 2,540,253) discloses the use of PEG to form granules suitable for the preparation of tablets. Rieglman et al. (U.S. Pat. No. 4,151,273) discloses a method of enhancing systemic absorption of poorly soluble drugs by forming a glossy solid matrix of the carrier (PEG) and the drug. A solution of the drug and the carrier is formed at an elevated temperature, with or without a solvent, and chilled rapidly to form a solid mass which can be ground to a powder.

Leeson (U.S. Pat. No. 3,862,311) discloses increased absorption of drugs when they are combined with carrier (PEG) and surfactant. See Col. 2, lines 3-9 and Col. 2, lines 48-58 for discussion of carriers used and of drug-surfactant-carrier ratios, respectively. Halpern et al. (U.S. Pat. No. 2,698,822) disclose PEG used to increase systemic absorption of insoluble drugs. Lowry et al. (U.S. Pat. No. 3,308,217) disclose a dry granulation method of preparing a mix for producing tablets using PEG (See Col. 4, lines 36-44), which employs a heating step. Chapura (U.S. Pat. No. 3,932,613) claims a PEG suppository.

SUMMARY OF THE INVENTION

In a composition aspect, this invention relates to ingestible granulated psyllium compositions consisting essentially of granules of psyllium powder rendered rapidly dispersible in water by the presence on the surface of the psyllium particles of a coating of an amount of a non-toxic, normally solid, alcohol soluble water dispersible polyethylene glycol, polyvinylpyrrolidone, or mixture thereof, effective to render the psyllium particles substantially instantly and uniformly dispersible in water. In a preferred aspect, the coating consists predominantly of polyethylene glycol plus an amount of polyvinyl pyrrolidone effective to reduce the friability of the granules.

In a method aspect, this invention relates to a method for rendering ingestible psyllium powder substantially instantly and uniformly dispersible in water which comprises wet granulating the psyllium powder with an amount of a solution in a volatile organic solvent, or mixture thereof with water, of a non-toxic, normally solid, alcohol soluble water dispersible polyethylene glycol, polyvinylpyrrolidone, or both, effective to render the granules when dry substantially instantly and uniformly dispersible in water. In a preferred aspect, the solvent is anhydrous ethanol.

DETAILED DISCUSSION

The psyllium powders employed in this invention are the conventional powders used commercially as such and to produce the prior art granulated compositions described hereinbefore.

Similarly, the wet granulation process of this invention employs procedures well known in the art. See e.g., U.S. Pat. No. 2,820,741 and references cited therein; U.S. Pat. No. 2,540,253; 2,980,589; and Newitt, D. M. et al. Proc. Fert. Soc., 1960, No. 55, pp. 1-35.

The polymers employed in this invention are the nontoxic, normally solid (under ambient conditions) alcohol soluble, water dispersible polymers of ethylene glycol and of vinylpyrrolidone. Such polymers are well known in the art. Such polyethylene glycols have somewhat lower molecular weights than the polyvinylpyrrolidones having substantially the same solubilities. The commercially available polyethylene glycols having the desired properties have molecular weights ranging from about 900 to about 20,000. The normally liquid polymers having lower molecular weights are less effective than the normally solid polymers. Preferred are those having a molecular weight from about 3,000 to 8,000. A particularly useful polymer (PEG 3350) has an average molecular weight of about 3,350. Included in the polyethylene glycols which can be employed in this invention are those whose terminal hydroxy groups have been chemically modified, e.g., by an ether or ester group. The commercially available polyvinylpyrrolidones having the desired properties have molecular weights ranging from about 10,000 to 360,000. A particularly useful polymer (Povidone K29/32) has a molecular weight of about 40,000. Contemplated equivalents of these polymers are corresponding copolymers and terpolymers having substantially the same physical characteristics.

Surprisingly, the polyethylene glycols for the most part are superior to the polyvinylpyrrolidones in their ability to produce psyllium granules which are substantially instantly wettable, i.e., which are completely wetted within 10 seconds in the wetting test described hereinafter. Therefore, the coating on the psyllium particles of the preferred compositions of this invention comprise and more preferably consist predominantly, i.e., more than 50% by weight, and most preferably consist of about 65-100% by weight, of polyethylene glycol.

Although psyllium granules coated solely with PEG have the fastest wetting times, the granules are rather frangible and tend to break up with handling or shipping. When the coating consists of a minor proportion, i.e., less than 50%, preferably about 10-35%, and most preferably about 15-25%, e.g., about 20%, of PVP, friability is reduced substantially without significantly affecting wettability rates.

The amount of PEG, PVP or mixture thereof present in the compositions of this invention varies somewhat with the particular polymers employed. Usually, however, 5% by weight of the granulated compositions is sufficient to impart substantially instantaneous, i.e., within 10 seconds, water wettability to the psyllium granules. Higher percentages ordinarily impart no further benefits to the compositions. The minimum amount required to do so ordinarily is at least 2%.

As would be expected, minor amounts of other polymers or other ingredients in the coating of the compositions can be tolerated without destroying the operability of the coating in rendering the psyllium granules substantially instantly and uniformly dispersible in water. However, such other materials do not ordinarily impart any benefits to the compositions and usually have an adverse effect thereon. Therefore, their presence therein is not ordinarily desirable.

The granulated psyllium compositions of this invention consist substantially entirely, i.e., at least about 90%, preferably about 92.5-97.5%, e.g., about 95%, by weight, of powdered psyllium.

In carrying out the method of this invention, the starting psyllium powder is wet granulated with a volatile organic solvent, e.g., the lower alkanols, e.g., methanol, ethanol, isopropanol and n-butanol, ketones, e.g., acetone and methylethyl ketone, ethers and esters. Because of residue problems, ethanol or 95% ethanol and 5% methanol is preferred. Substantially anhydrous solvents, i.e., no more than about 10% water, are preferred because the presence of a significant proportion of water tends to have an adverse effect on the drying times and/or the wettability of the psyllium granules produced therefrom, generally directly proportion to the amount of water in the solvent. However, an amount of water in the organic solvent which does not significantly transfer from the solvent phase to the psyllium, e.g., up to about 50% by volume but preferably less than 25% by volume, generally can be tolerated in the solvent without seriously affecting the water dispersibility of the psyllium granules produced therefrom.

The amount of solvent employed is preferably only that amount required to uniformly wet the psyllium particles, e.g., from about 5% to 25%, preferably about 7-15%, by weight thereof. Larger amounts of solvent have no advantage and tend to complicate the wet granulation process. Lesser amounts tend to wet the psyllium particles unevenly, producing granules which produce lumps when dispersed in water.

The proportion of polymer or mixture of polymers to solvent employed in the wet granulation process depends primarily upon the amount of polymer desired to be deposited on the polymers, assuming an amount of solvent in excess of that required to wet the psyllium is not employed. Generally, a solvent to polymer ratio from about 3:1 to 1:1, preferably about 2:1, by weight is employed.

The psyllium powder is then wet granulated in a conventional manner with an amount of the polymer solution sufficient to uniformly wet the psyllium particles and to deposit thereon the desired amount of polymer or mixture of polymers, viz., by gradually adding the solution to the psyllium powder with continuous agitation. When all of the solution has been added, the thus-produced wet granules are dried of solvent, preferably without agitation, e.g., in trays in a drying room with exhaust fans to discharge the evaporated solvent. If desired, the granules can then be screened to desired particle size distribution, e.g., through a No. 20 mesh screen. The dry granulated particles can then be packaged conventionally, e.g., unit dose pouches or 250 g. bottles.

In addition to being substantially instantly and uniformly dispersible in water, the granulated psyllium compositions of this invention can readily be dispersed in aqueous beverages, e.g., prune juice, tomato juice, orange and other fruit juices, fruit flavored soft drinks, milk, coffee and tea, the limitations being dictated primarily by palatability considerations rather than rapid dispersibility.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE I 5.331 kg of powdered polyvinylpyrrolidone (Povidone K29/32) and 21.613 kg of powdered polyethylene glycol (P.E.G. 3350) was dissolved in 50 kg of anhydrous 95% ethanol/5% methanol with warming to 50° C. until the polymers dissolved therein. The solution was pumped onto 500 kg of tumbling psyllium powder. The wet granules which formed were spread onto drying trays, where they were dried overnight. Screening the dry granules through a No. 14 mesh screen yielded a uniform essentially powder-free granulated product which resists crumbling during shipping and handling and which rapidly (in less than 10 seconds) disperses without lumping in water.

EXAMPLE II

In the examples which follow, unless indicated otherwise, the granulated psyllium compositions were produced from 475 g of powdered psyllium seed husks and a solution of powdered polyethylene glycol of an average molecular weight of 3,350 (P.E.G. 3350) and/or polyvinylpyrrolidone of an average molecular weight of 40,000 ("Povidone K29/32"), in 60 ml anhydrous ethanol denatured with 5% w/w methanol (SDA-3A) by dissolving the polymer in the ethanol with heating, charging the powdered psyllium in a Hobart mixer; wet granulating by gradually adding the polymer solution to the psyllium while the latter is agitated in the mixer and mixing for one minute; spreading the wet granules out on a tray and drying overnight at room temperature and sizing the dried granules through No. 20 mesh screen.

Wettability of the dry granules was determined according to the wetting test described above. Friability of the dry granules was determined on a Cenco Meinzer Sieve Shaker (speed No. 4) containing 535 glass beads each weighing about 0.17 g. and having a diameter of 0.195 inch. 80 grams of the dry granules retained on a 60 mesh screen were placed on the 60 mesh screen along with the glass beads and the shaker run for either 2 or 4 minutes and the percentage of under 60 mesh granules determined.

| Example | Granulating Solvent (wt. %) EtOH + MeOH | H$_2$O | Polymer P.E.G. | P.V.P. | Other | Wetting Time (sec.) | Friability (% under 60 mesh) 2 min. | 4 min. |
|---|---|---|---|---|---|---|---|---|
| IIa | 100% | — | 5 | | | 0.8 | 3.38 | 6.50 |
| b | " | — | 4 | | | 0.9 | 6.88 | 11.88 |
| c | " | — | 3 | | | 1 | 7.81 | 14.06 |
| d | " | — | 2 | | | 1.6 | 9.75 | 16.75 |
| e | " | — | 4.5 | 0.5 | | 1 | 3.00 | 5.13 |
| f | " | — | 4 | 1 | | 1 | 2.94 | 4.81 |
| g | 62.5 | 37.5 | 4 | 1 | | 3.2 | 8.75 | 14.63 |
| h | 100% | — | 3 | 2 | | 1.8 | 2.13 | 3.88 |
| i | " | — | 3.2 | 0.8 | | 1 | 2.38 | 5.00 |
| j | " | — | 2.4 | 0.6 | | 1.2 | 5.60 | 9.50 |
| k | " | — | 1.6 | 0.4 | | 1.8 | 8.50 | 14.63 |
| l | " | — | 2 | 3 | | 2 | 1.88 | 3.13 |
| m | " | — | 1 | 4 | | 2 | 2.00 | 3.38 |
| n | " | — | 4$^a$ | 1 | | 1 | | |
| o | " | — | 4$^b$ | 1 | | 11 | | |
| p | " | — | | 5 | | 5.4 | 2.63 | 5.25 |
| q | " | — | | 4 | | 5.6 | 4.60 | 7.50 |
| r | " | — | | 3 | | 6.2 | 4.75 | 8.75 |
| s | " | — | | 2 | | 7.5 | 6.00 | 13.13 |
| t | 82.5 | 17.5* | 4 | | 1 (sucrose) | 2 | 8.9 | 14.70 |
| u | 37.5 | 62.5* | 4 | | 1 (gelatin) | 8 | 9.75 | 14.5 |
| v | 31.4 | 68.6* | 4 | | 1 (acacia) | 7 | 6.63 | 10.0 |
| w | 60 | 40* | 4 | | 1 (methocel) | 8 | 11.25 | 18.38 |

$^a$P.E.G. 8000
$^b$P.E.G. 600
*min. required to produce clear solution

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An ingestible granulated psyllium composition consisting essentially of granules of psyllium powder and having at least 90% psyllium content, rendered rapidly dispersible in water by the presence on the surface of the psyllium particles of a coating of an amount up to about 10% by weight of a non-toxic, normally solid, alcohol soluble, water dispersible polyethylene glycol, polyvinylpyrrolidone, or mixture thereof, effective to render the psyllium particles substantially instantly and uniformly dispersible in water.

2. A composition according to claim 1 wherein the coating comprises polyethylene glycol.

3. A composition according to claim 1 whose coating consists predominantly of about 2 to about 5% by weight of the composition of polyethylene glycol.

4. A composition according to claim 2 wherein the polyethylene glycol has a molecular weight from about 3,000 to 8,000.

5. A composition according to claim 2 wherein the coating on the psyllium particles contains an amount of polyvinylpyrrolidone effective to render the granules significantly less friable than correspondingly granulated psyllium coated with the same amount of the polyethylene glycol only.

6. A composition according to claim 5 containing about 2.5 to 4% by weight thereof of a polyethylene glycol and about 2 to 0.5% by weight thereof of polyvinylpyrrolidone.

7. A composition according to claim 6 wherein the polyethylene glycol has a molecular weight from about 3,000 to about 8,000.

8. A composition according to claim 7 containing about 4% by weight of polyethylene glycol and about 1% by weight of polyvinylpyrrolidone.

9. A composition according to claim 8 wherein the polyethylene glycol has a molecular weight of about 3,350.

10. A method for rendering ingestible psyllium powder substantially instantly and uniformly dispersible in water which comprises wet granulating and psyllium powder with an amount of a solution in a volatile organic solvent, or mixture thereof with water, of up to 10% by weight of the psyllium of a non-toxic, normally solid, alcohol soluble, water dispersible polyethylene glycol, polyvinylpyrrolidone, or both, effective to render the granules when dry substantially instantly and uniformly dispersible in water.

11. A method according to claim 10 wherein the solvent is anhydrous.

12. A method according to claim 10 wherein the solvent consists at least about 95% of ethanol.

13. A method according to claim 10 wherein the solution comprises polyethylene glycol.

14. A method according to claim 13 wherein the solution also contains an amount of polyvinylpyrrolidone effective to render the granules less friable than corresponding granules produced from a solution of the same amount of the polyethylene glycol alone.

15. A method according to claim 13 wherein the solvent is anhydrous.

16. A method according to claim 15 wherein the solvent consists at least about 95% of ethanol.

* * * * *